United States Patent [19]

Dümler et al.

[11] Patent Number: 5,869,030
[45] Date of Patent: Feb. 9, 1999

[54] SUNSCREEN COMPOSITIONS COMPRISING MICRONIZED, INSOLUBLE ORGANIC UV ABSORBERS

[75] Inventors: Walter Dümler, Bad Bellingen-Hertin, Germany; Peter Frankhauser, Ettingen, Switzerland; Helmut Luther, Grenzach-Wyhlen, Germany

[73] Assignee: Ciba Specialty Chemicals Corporation, Tarrytown, N.Y.

[21] Appl. No.: 693,080

[22] PCT Filed: Feb. 11, 1995

[86] PCT No.: PCT/EP95/00501

§ 371 Date: Aug. 12, 1996

§ 102(e) Date: Aug. 12, 1996

[87] PCT Pub. No.: WO95/22959

PCT Pub. Date: Aug. 31, 1995

[30] Foreign Application Priority Data

Feb. 23, 1994 [GB] United Kingdom ............. 9403451

[51] Int. Cl.⁶ ............. A61K 7/42; A61K 31/53; A61K 7/00
[52] U.S. Cl. ............. 424/59; 424/60; 424/400; 424/401; 514/241
[58] Field of Search ............. 424/59, 60, 400, 424/401; 544/197; 514/241, 242

[56] References Cited

U.S. PATENT DOCUMENTS

| | | | |
|---|---|---|---|
| 3,004,896 | 10/1961 | Heller et al. | 167/90 |
| 4,514,383 | 4/1985 | Murray et al. | 424/59 |
| 4,617,390 | 10/1986 | Hoppe et al. | 544/197 |

FOREIGN PATENT DOCUMENTS

| | | |
|---|---|---|
| A-87098 | 8/1983 | European Pat. Off. . |
| A-517104 | 12/1992 | European Pat. Off. . |
| A-649841 | 4/1995 | European Pat. Off. . |
| 2194442 | 3/1974 | France . |
| 2282462 | 3/1976 | France . |
| 2526313 | 11/1983 | France . |
| 2681329 | 3/1993 | France . |
| 4105923 | 8/1992 | Germany . |
| A-480090 | 12/1969 | Switzerland . |
| A-480091 | 12/1969 | Switzerland . |
| 2227410 | 8/1990 | United Kingdom . |
| 92/13517 | 8/1992 | WIPO . |
| 93/18744 | 9/1993 | WIPO . |
| 94/05645 | 3/1994 | WIPO . |

OTHER PUBLICATIONS

Redox Mechanisms in Heterogeneous Photocatalysis, Serpone et al.

*Primary Examiner*—Shelley A. Dodson
*Attorney, Agent, or Firm*—Kevin T. Mansfield

[57] ABSTRACT

The present invention provides a micronised, insoluble organic UV absorber which is especially suitable for use in pharmaceutical or cosmetic applications, with the exclusion of o-hydroxyphenyl-s-triazines having formula (I) in which $R_a$, $R_b$ and $R_c$, independently, are hydrogen, halogen, $C_1$–$C_{18}$alkyl or $C_1$–$C_{18}$alkoxy, and $R_d$ and $R_e$, independently, are hydrogen or $C_1$–$C_{18}$alkoxy, with the provisos that one of $R_d$ and $R_e$ is always $C_1$–$C_{18}$alkoxy, and that, if $R_b$, $R_c$, $R_d$ and $R_e$ are each $C_1$–$C_{18}$alkoxy, then $R_a$ is halogen, $C_1$–$C_{18}$alkyl or $C_1$–$C_{18}$alkoxy; and a sunscreen composition comprising the micronised, insoluble organic UV absorber together with a cosmetically compatible carrier. The UV absorber is of the oxalamide, triazine, vinylgroup containing amide or cinnamic acid amide classes.

42 Claims, No Drawings

SUNSCREEN COMPOSITIONS COMPRISING MICRONIZED, INSOLUBLE ORGANIC UV ABSORBERS

The present invention relates to new physical forms of UV absorbers and to their use in sunscreen compositions which, in turn, are useful, in particular, for the protection of human skin.

It has long been known that prolonged exposure to that UV radiation which reaches the surface of the earth can lead to the formation of erythemas or light dermatoses, as well as to an increased incidence of skin cancers or accelerated skin aging.

Various sunscreen formulations have been proposed which include a material which is intended to counteract UV radiation, thereby inhibiting the said undesired effects on the skin.

A great number of compounds has been proposed for use as UV protectants in sunscreen formulations, especially soluble organic UV absorbers and insoluble micronised inorganic compounds, in particular zinc oxide and titanium dioxide.

With respect to the use in sunscreen formulations of soluble organic UV absorbers, they have disadvantages that their effectiveness as UV protectants in terms of SPF (Sun Protection Factor) in a sunscreen formulation is often too low for commercial purposes; as a result of their solubility, they exhibit relatively high allergenic potential; and that as a result of intrinsic photochemical lability, the duration of the protective effect is often too low.

The high specific weight of insoluble inorganic compounds, such as zinc oxide and titanium dioxide leads to a reduced stability of formulations containing them. Moreover, such inorganic compounds have been claimed to generate toxic radicals under the influence of light ("Redox Mechanisms in Heterogeneous Photocatalysis", Serpone et al, Electrochemistry in Colloids and Dispersions, Editors Mackay and Texter, VCH Publishers Inc., New York 1992).

It has now been found, surprisingly, that micronised, insoluble organic UV absorbers, when used in sunscreen formulations, provide excellent UV protection and have at least as high an SPF rating as corresponding sunscreen formulations containing a known inorganic UV absorber. Unlike the latter UV absorbers, micronised, insoluble organic UV absorbers show no tendency, under the influence of light, to generate radicals which could damage or sensitise human skin. Moreover due to their insolubility in sunscreen formulations, micronised, insoluble organic UV absorbers do not penetrate the skin so that they are not able to exert any undesired allergic or sensitising effects on the skin.

Accordingly, the present invention provides, as a first aspect, a composition of matter, which is especially suitable for use in pharmaceutical or cosmetic applications, comprising a micronised, insoluble organic UV absorber, with the exclusion of o-hydroxyphenyl-s-triazines having the formula:

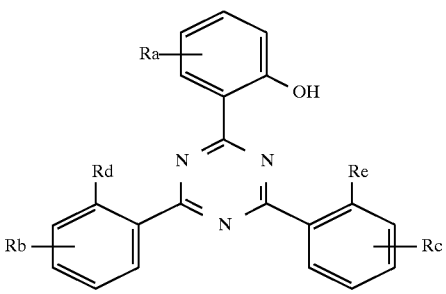

in which $R_a$, $R_b$ and $R_c$, independently, are hydrogen, halogen, $C_1-C_{18}$alkyl or $C_1-C_{18}$alkoxy, and $R_d$ and $R_e$, independently, are hydrogen or $C_1-C_{18}$alkoxy with the provisos that one of $R_d$ and $R_e$ is always $C_1-C_{18}$alkoxy, and that, if $R_b$, $R_c$, $R_d$ and $R_e$ are each $C_1-C_{18}$alkoxy, then $R_a$ is halogen, $C_1-C_{18}$alkyl or $C_1-C_{18}$alkoxy.

Preferably, the insoluble organic UV absorber has a mean particle size in the range of from 0.02 to 2, more preferably from 0.05 to 1.5, especially from 0.1 to 1.0μ.

The insoluble organic UV absorber may be converted into the desired particulate size state by conventional methods, e.g. by grinding the insoluble organic UV absorber, in coarse particle form, in the presence of suitable grinding aids and using known grinding apparatus, e.g., a jet, ball, vibration or hammer mill, preferably a high speed stirring mill or impact mill, especially a rotating ball mill, vibrating mill, tube mill or rod mill.

Preferably, the grinding is conducted in the presence of 0.1 to 30%, preferably 0.5 to 15% by weight, based on the micronised, insoluble organic UV absorber, of a grinding aid such as an alkylated vinylpyrrolidone polymer, a vinylpyrrolidone-vinylacetate copolymer, an acylglutamate, an acrylate-tert.-octylpropenamide copolymer, a ditolylether sulphonic acid-formaldehyde condensate, a Carbomer, a commercial mixture of fatty acid esters comprising a nonionic precurser such as tristyrylphenol ethoxylate or, in particular, a phospholipid.

Preferred insoluble UV absorbers for use in the present invention include those of the oxalanilide, triazine, triazole, vinyl group-containing amide or cinnamic acid amide classes.

One preferred class of oxalanilide UV absorbers is that having the formula:

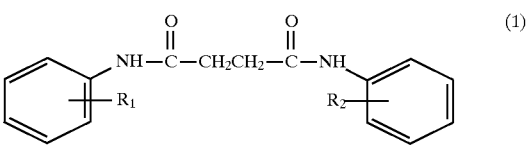

in which $R_1$ and $R_2$, independently are $C_1-C_{18}$alkyl or $C_1-C_{18}$alkoxy.

One preferred class of triazine UV absorbers is that having the formula:

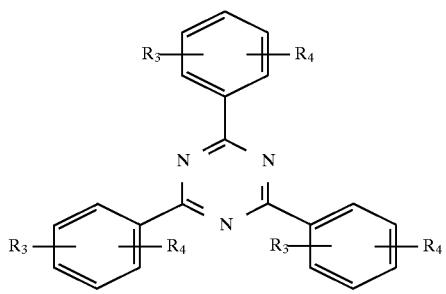

in which $R_3$ and $R_4$, independently, are hydrogen, hydroxy or $C_1$–$C_5$alkoxy, preferably hydrogen hydroxy or methoxy, with the exclusion of o-hydroxyphenyl-s-triazines having the formula:

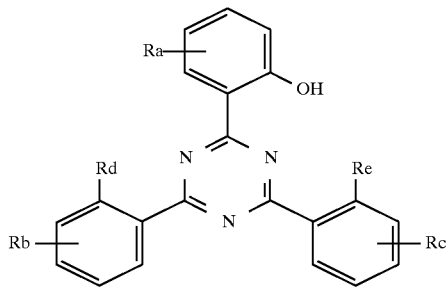

in which $R_a$, $R_b$ and $R_c$, independently, are hydrogen, halogen, $C_1$–$C_{18}$alkyl or $C_1$–$C_{18}$alkoxy, and $R_d$ and $R_e$, independently, are hydrogen or $C_1$–$C_{18}$alkoxy, with the provisos that one of $R_d$ and $R_e$ is always $C_1$–$C_{18}$alkoxy, and that, if $R_b$, $R_c$, $R_d$ and $R_e$ are each $C_1$–$C_{18}$alkoxy, then $R_a$ is halogen, $C_1$–$C_{18}$alkyl or $C_1$–$C_{18}$alkoxy.

A second preferred class of triazine UV absorbers is that having the formula:

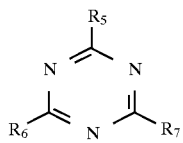

in which $R_5$, $R_6$ and $R_7$, independently, are H, OH, $C_1$–$C_{18}$alkoxy, $NH_2$, NH—$R_8$ or $N(R_8)_2$ in which $R_8$ is $C_1$–$C_{18}$alkyl, $OR_8$ in which $R_8$ has its previous significance, phenyl, phenoxy or anilino in which the respective phenyl moieties are optionally substituted by one, two or three substitutents selected from OH, $C_1$–$C_{18}$alkyl or -alkoxy $C_5$–$C_8$cycloalkyl, a methylidenecamphor group, a group —(CH═CH)$_n$C(═O)—$OR_8$ in which n is 0 or 1 and $R_8$ has its previous significance or a

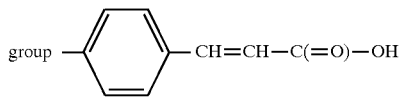

or the corresponding alkali metal, ammonium, mono-, di- or tri-$C_1$–$C_4$alkylammonium mono-, di- or tri-$C_2$–$C_4$alkanolammonium salts, or the $C_1$–$C_{18}$alkyl esters thereof.

One preferred class of triazole UV absorbers is that having the formula:

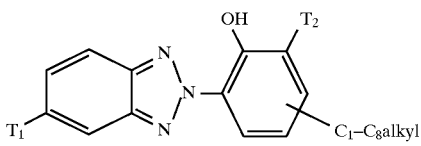

in which $T_1$ is $C_1$–$C_{18}$alkyl, or preferably hydrogen; and $T_2$ is $C_1$–$C_{18}$alkyl optionally substituted by a phenyl group.

A further preferred class of triazole UV absorbers is that having the formula:

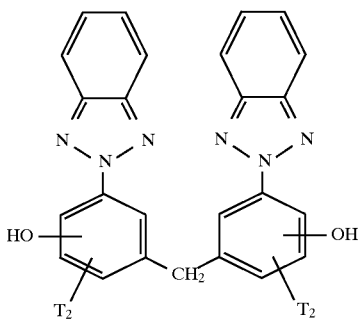

in which $T_2$ has its previous significance.

A preferred class of vinyl group-containing amide UV absorbers is that having the formula:

$$R_9\text{-}(Y)_n\text{—}C(=O)\text{—}C(R_{10})=C(R_{11})\text{—}N(R_{12})(R_{13}) \qquad (6)$$

in which $R_9$ is $C_1$–$C_{18}$alkyl preferably, $C_1$–$C_5$alkyl or phenyl in which the phenyl is optionally substituted by one, two or three substituents selected from OH, $C_1$–$C_{18}$alkyl or -alkoxy or a group —C(═O)—$OR_8$ in which $R_8$ has its previous significance; $R_{10}$ and $R_{11}$ are the same or different and each is $C_1$–$C_{18}$alkyl, preferably $C_1$–$C_5$alkyl or hydrogen; $R_{12}$ and $R_{13}$ are the same or different and each is $C_1$–$C_{18}$alkyl, preferably $C_1$–$C_5$alkyl or hydrogen: Y is N or O; and n is 0 or 1.

A preferred class of cinnamic acid amide UV absorbers is that having the formula:

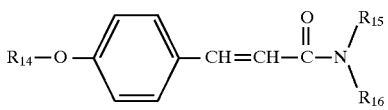

in which $R_{14}$ is hydroxy or O—$C_1$–$C_4$alkyl, preferably methoxy or ethoxy; $R_{15}$ is hydrogen or $C_1$–$C_4$alkyl, preferably methyl or ethyl; and $R_{16}$ is —(CONH)$_n$-phenyl in which n is 0 or 1 and the phenyl is optionally substituted by one, two or three substituents selected from OH, $C_1$–$C_{18}$alkyl or -alkoxy or a group —C(═O)—$OR_8$ in which $R_8$ has its previous significance. Preferably $R_{16}$ is a phenyl, 4-methoxyphenyl or phenylaminocarbonyl group.

In the compounds of formulae (1) to (7), $C_1$–$C_{18}$alkyl groups may be methyl, ethyl, n-propyl, isopropyl, n-butyl, isobutyl, tert.-butyl, n-amyl, n-hexyl, n-heptyl, n-octyl, isooctyl, n-nonyl, n-decyl, n-undecyl, n-dodecyl, tetradecyl, hexydecyl or octadecyl.

$C_1$–$C_{18}$alkoxy groups include methoxy, ethoxy, propoxy, butoxy, n-hexoxy, n-heptoxy, n-octoxy, isooctoxy, n-nonoxy, n-decoxy, n-undecoxy, n-dodecoxy, tetradecoxy, hexadecoxy or octadecoxy, methoxy and ethoxy being preferred.

$C_5$–$C_8$cycloalkyl includes cyclopentyl, cyclohexyl and cyclooctyl.

One particularly preferred compound of formula (1) is N-(2-ethoxyphenyl)-N'-(2-ethylphenyl)-ethanediamide.

Preferred compounds of formula (2) are those having the formulae:

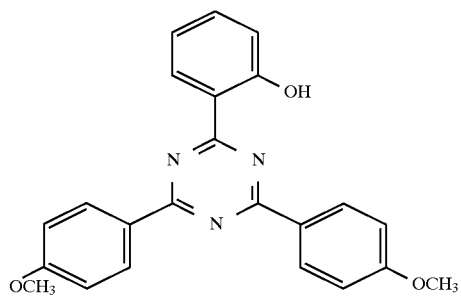 (8)
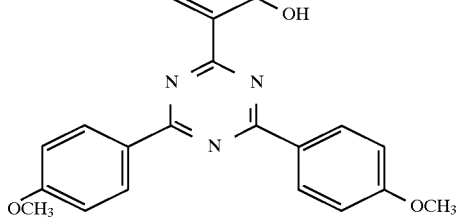 (13)
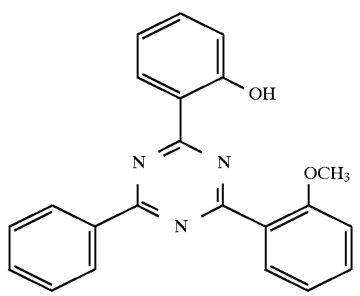 (9)
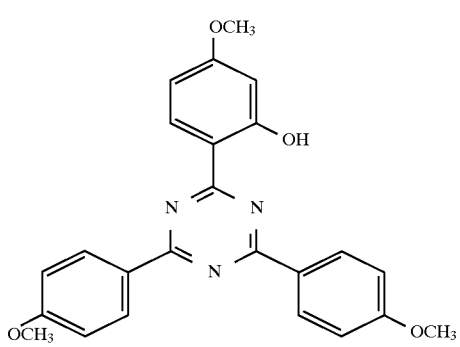 (14)
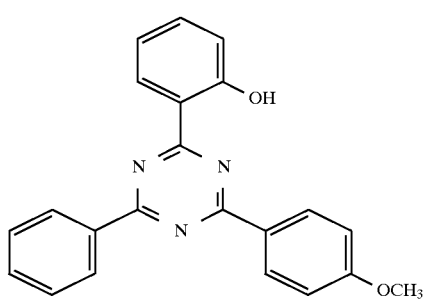 (10)
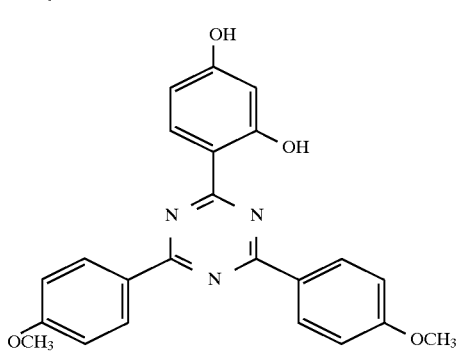 (15)
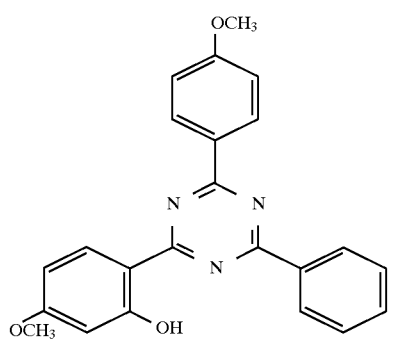 (11)
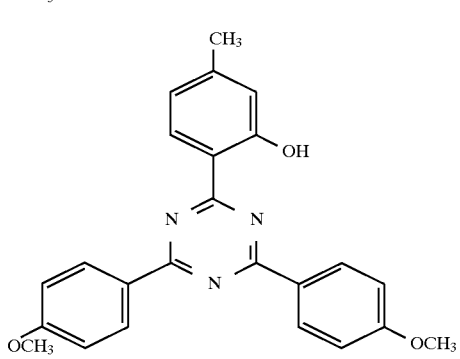 (16)
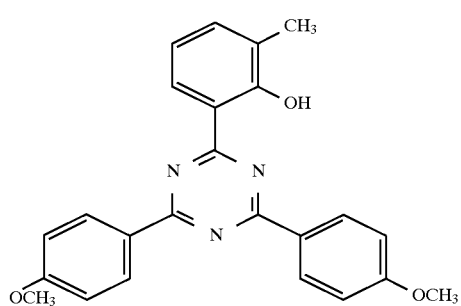 (12)
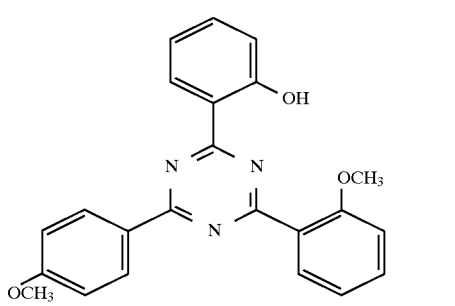 (17)

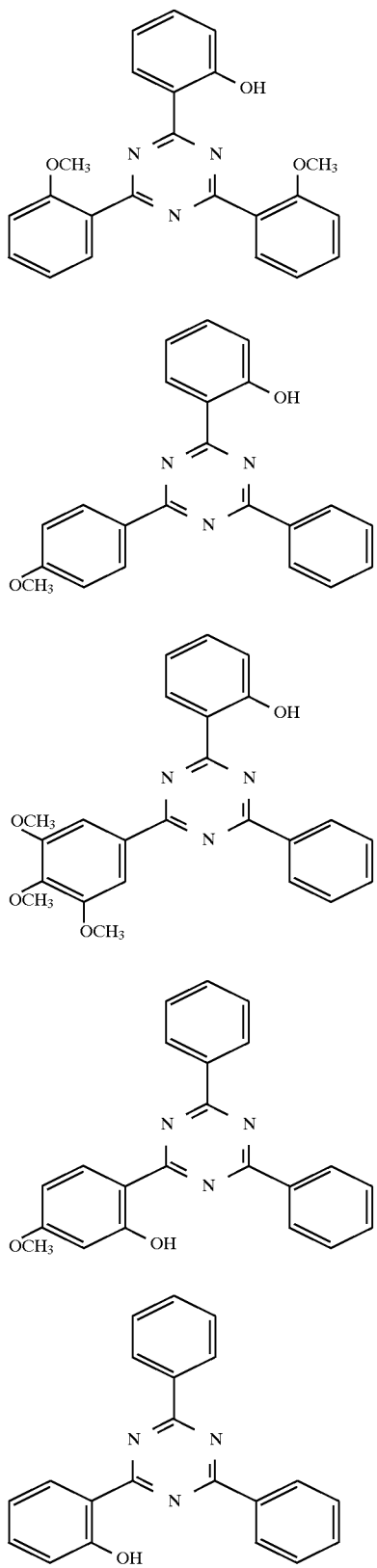
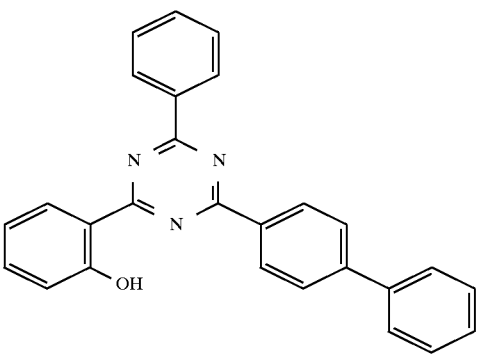
as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.
A preferred compound of formula (3) is that having the formula:
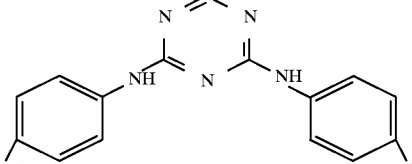
Preferred compounds of formula (4) include those having the formulae:
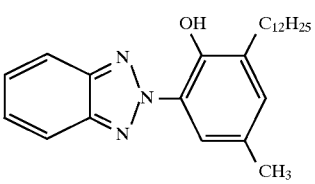
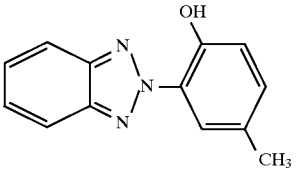

-continued

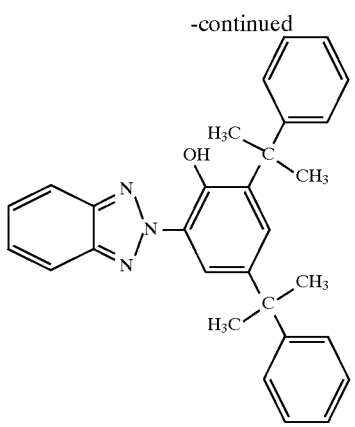
(27)

A preferred compound of formula (5) is that having the formula:

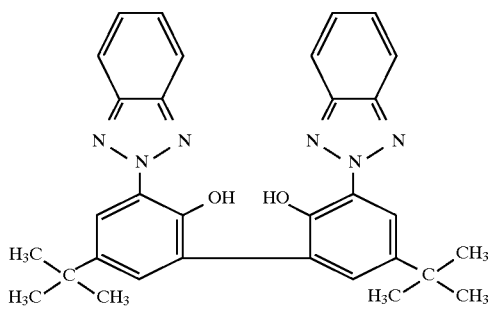
(28)

Specific examples of preferred compounds of formula (6) include
4-octylamino-3-penten-2-one
ethyl-3-octylamino-2-butenoate
3-octylamino-1-phenyl-2-buten-1-one and
3-dodecylamino-1-phenyl-2-buten-1-one.

The compounds of formula (1) to (7) are known and may be prepared known methods.

The micronised, insoluble organic UV absorber may be used together with one or more UV absorbers which are conventionally used in cosmetic compositions for the protection of human skin against UV radiation.

The phospholipid, used as the preferred grinding aid in the production of the micronised, insoluble organic UV absorber of the present invention, may be of natural or synthetic origin. Naturally occuring phospholipids include phosphatidyl cholines, phosphatidyl serines, phosphatidyl inositols, phosphatidyl ethanolamines, diphosphatidyl glycerols and sphingomyelins which are obtainable from such natural sources as mammalian liver tissue, egg yolk, soybean etc. Synthetic phospholipids may be produced from natural oils such as rapeseed oil. The oil may be hydrogenated, selectively esterified and phosphorylated to form either specific phosphatidates or mixtures of these.

As already indicated, the composition of the present invention is particularly suitable for use in a sunscreen formulation.

Accordingly, the present invention also provides a sunscreen composition comprising a) 0.1 to 15%, preferably 0.5 to 10% by weight, based on the total composition of a micronised, insoluble organic UV absorber; and b) a cosmetically acceptable carrier.

The sunscreen composition of the present invention may be produced by physically blending the micronised, insoluble organic UV absorber and carrier components by any conventional method, e.g. by simply stirring the two materials together. In a preferred procedure, a mixture of the coarse, insoluble organic UV absorber, the grinding aid, preferably a phospholipid and the milling bodies are ground until the coarse, insoluble organic UV absorber has been converted into micronised form, as described earlier in relation to the production of the micronised, insoluble organic UV absorber. After filtering off the milling bodies, e.g. quartz sand or glass balls, the filtrate, consisting of the micronised, insoluble organic UV absorber and grinding aid components, may be blended with a cosmetically compatible carrier.

The sunscreen composition of the invention may be formulated as a water-in oil or an oil-in-water emulsion, an oil or oil-alcohol lotion a vesicular dispersion of an ionic or nonionic amphiphilic lipid, a gel, a solid stick or an aerosol formulation.

When formulated as a water-in oil or an oil-in-water emulsion, the cosmetically acceptable carrier preferably comprises 5 to 50% of an oil phase, 5 to 20% of an emulsifier and 30 to 90% of water, each by weight based on the total weight of the carrier.

The oil phase may comprise any oil conventionally used in cosmetic formulations, e.g., one or more of a hydrocarbon oil, a wax, a natural oil, a silicone oil, a fatty acid ester or a fatty alcohol. Preferred mono- or polyols are ethanol, isopropanol, propylene glycol, hexylene glycol, glycerine and sorbitol.

The emulsifier also may comprise any emulsifier conventionally used in cosmetic formulations, e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The sunscreen composition of the invention may also comprise further components which are known to perform a useful function in a sunscreen composition. Examples of such further components, include, e.g., emollients, skin moisturisers, skin tanning accelerators, emulsion stabilisers, thickening agents such as xanthan, moisture-retention agents such as glycerine, film formers, preservatives, perfumes and colourants.

The sunscreen composition of the invention provides excellent protection of the human against the damaging effects of sunlight, while permitting safe tanning of the skin. Moreover, the sunscreen composition of the invention has a skin waterproofing effect.

The following Examples further illustrate the present invention.

EXAMPLE 1

12.8 g of 2,4,6-trianilino-p-(carbo-2'-ethylhexyl-1'-oxy)-1,3,5-triazine having the formula:

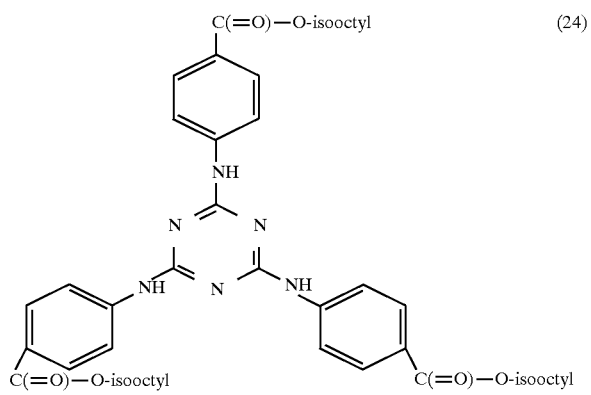

12,8 g of a commercially-available phospholipid (Phospholipon 90®), 135 g of water and 130 mls of glass beads of 3 mm diameter are ground in an abrasion-resistant container, at 300 rpm for 8 hours, using a suitable stirrer. The resulting suspension is separated from the grinding beads by suction filtration. The mean particle size diameter of ground material so obtained is 0.96μ, the particle size range being from 0.4 to 1.7μ.

EXAMPLE 2

The suspension obtained in Example 1 is used to produce a cream having the following composition:

| Phase A | |
|---|---|
| Abil WE 09 (polysiloxane-alkylene-polyether copolymer) | 5.00% |
| Paraffin | 8.00% |
| Emulsifier ($C_{12}/C_{14}$-fatty acid-2-ethylhexyl ester) | 5.00% |
| Microwax 7694 | 4.00% |
| Suspension from Example 1 | 30.00% |
| Propylhydroxy benzoate | 0.10% |
| Antioxidant | 0.03% |
| Phase B | |
| Glycerol | 3.00% |
| Methylhydroxy benzoate | 0.20% |
| Phase C | |
| Water | 35.82% |
| Sodium chloride | 0.80% |
| Phase D | |
| Kathon CG (stabiliser) | 0.05% |
| | 100.00% |

Phase A is prepared and heated to 70° C. Phase B and C, which have been heated to 70° C., are added slowly while stirring the mixture using a high speed stirrer operating at 12,000 rpm. The emulsion so formed is cooled to 40° C. and, while it is stirred, using a slow speed stirrer operating at 60 rpm, phase D is added. The emulsion is cooled further to 25° C. and then re-homogenised using a three roll mill.

The sunscreen factor of the homogenised emulsion is 2.4 when determined according to DIN 67501.

EXAMPLE 3

12.8 g of the UV absorber having the formula:

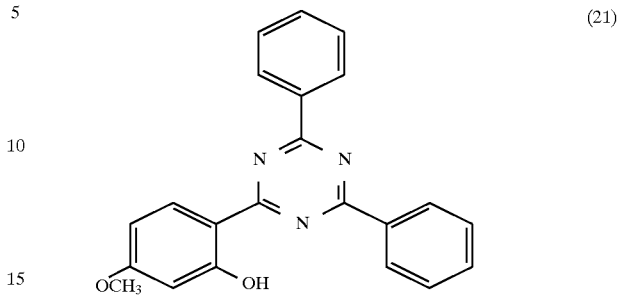

12.8 g of a commercially-available phospholipid (Phospholipon 90®), 135 g of water and 130 mls of grinding sand are ground in an abrasion-resistant container, at 900 rpm for 3 hours, using a suitable stirrer. The resulting suspension is separated from the grinding sand by suction filtration. The mean particle size diameter of ground material so obtained is 0.8μ, the particle size range being from 0.3 to 1.1μ.

The SPF values are determined for compounds (24) and (21) according to DIN 67501. Compounds (24) and (21) are firstly micronised to the same particle size characteristics and then incorporated, at a concentration of 3% by weight, into a standard water-in-oil emulsion. For the purpose of comparison titanium, dioxide is evaluated under the same conditions. The results obtained are set out below:

| UV Protectant | SPF Value |
|---|---|
| Titanium dioxide | 2.3 |
| Compound (24) | 2.4 |
| Compound (21) | 2.5 |

These results show that emulsions according to the present invention have SPF values which are at least as high as that obtained with $TiO_2$, without the potential toxicity hazards associated with the latter.

EXAMPLE 4

25 g of 2,2'-Methylene-bis-[6-(2H-benzotriazol)-2-yl)]-4-(1,1,3,3-tetramethylbutyl)-phenol, 5 g of Luviskol VA 64®, 75 g of water and 50 mls of zirconium beads are ground in an abrasion-resistant container, at 900 rpm for 60 hours, using a suitable stirrer. The resulting suspension is separated from the grinding beads by suction filtration. The mean particle size diameter of ground material so obtained is 0.15μ.

We claim:

1. A composition of matter, suitable for use in pharmaceutical or cosmetic compositions, consisting of a micronised, insoluble oxalanilide, triazine, triazole, vinyl group-containing amide or cinnamic acid amide organic UV absorber having a mean particle size in the range of from 0.02 to 2.0μ, with the exclusion of o-hydroxyphenyl-s-triazines having the formula:

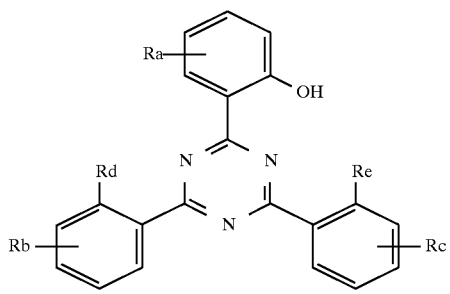

in which $R_a$, $R_b$ and $R_c$, independently, are hydrogen, halogen, $C_1$–$C_{18}$alkyl or $C_1$–$C_{18}$alkoxy, and $R_d$ and $R_e$, independently, are hydrogen or $C_1$–$C_{18}$alkoxy, with the provisos that one of $R_d$ and $R_e$ is always $C_1$–$C_{18}$alkoxy, and that, if $R_b$, $R_c$, $R_d$ and $R_e$ are each $C_1$–$C_{18}$alkoxy, then $R_a$ is halogen, $C_1$–$C_{18}$alkyl or $C_1$–$C_{18}$alkoxy.

2. A composition according to claim 1 in which the micronised, insoluble organic UV absorber has been produced by grinding the insoluble organic UV absorber, in coarse particulate form, in a grinding apparatus in the presence of a grinding aid, until the insoluble organic UV absorber has been converted into micronised form.

3. A composition according to claim 2 in which the grinding apparatus is a jet, ball, vibration or hammer mill.

4. A composition according to claim 2 in which the grinding aid is used in an amount of 0.1 to 30% by weight of the insoluble organic UV absorber.

5. A composition according to claim 2 in which the grinding aid is an alkylated vinylpyrrolidone polymer, a vinylpyrrolidone-vinylacetate copolymer, an acylglutamate, an acrylate-tert.-octylpropenamide copolymer, a ditolylether sulphonic acid-formaldehyde condensate, a Carbomer, a commercial mixture of fatty acid esters comprising a non-ionic precurser or a phospholipid.

6. A composition according to claim 5 in which the grinding aid is a phospholipid.

7. A composition according to claim 6 in which the phospholipid is one or more of a phosphatidyl choline, phosphatidyl serine, phosphatidyl inositol, phosphatidyl ethanolamine, diphosphatidyl glycerol or a sphingomyelin.

8. A composition according to claim 1 in which the UV absorber is an oxalanilide and has the formula:

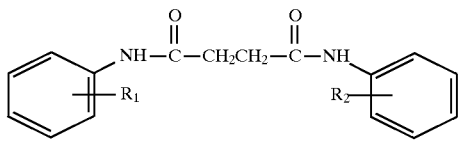

in which $R_1$ and $R_2$, independently are $C_1$–$C_{18}$alkyl or $C_1$–$C_{18}$alkoxy.

9. A composition according to claim 8 in which the UV absorber is N-(2-ethoxyphenyl)-N'-(2-ethylphenyl)-ethanediamide.

10. A composition according to claim 1 in which the UV absorber is a triazine and has the formula:

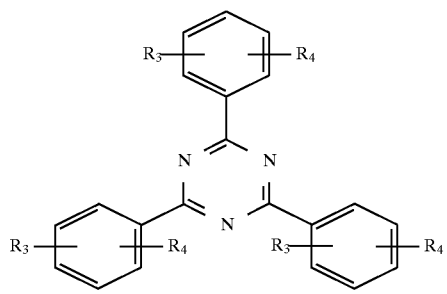

in which $R_3$ and $R_4$, independently, are hydrogen, hydroxy or $C_1$–$C_5$alkoxy.

11. A composition according to claim 10 in which $R_3$ and $R_4$, independently, are hydrogen, hydroxy or methoxy.

12. A composition according to claim 11 in which the UV absorber has the formula:

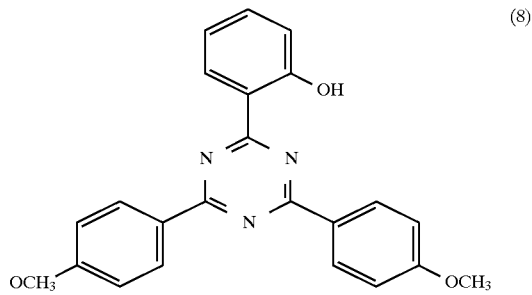

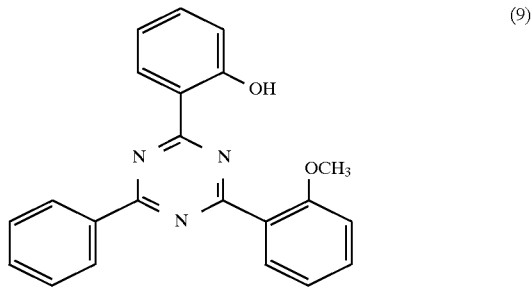

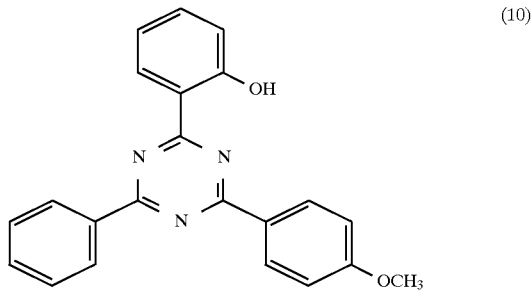

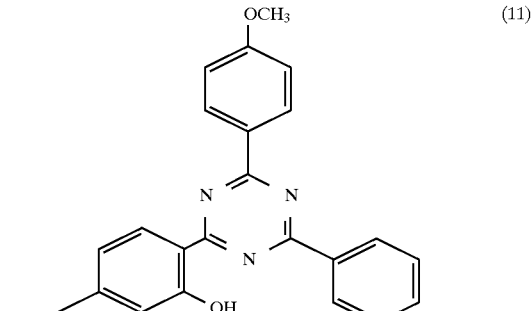

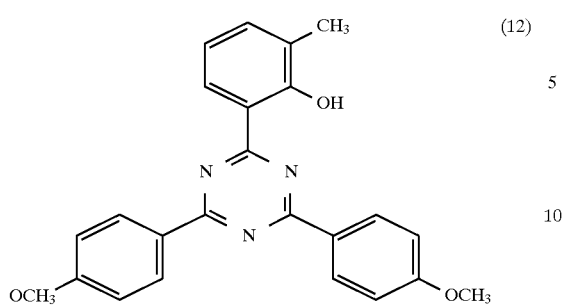
(12)
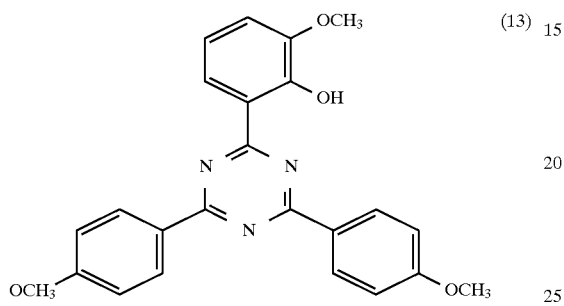
(13)
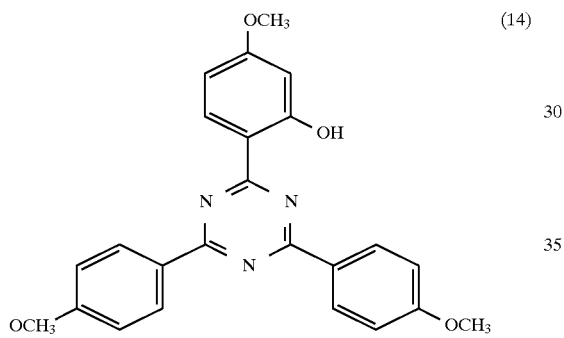
(14)
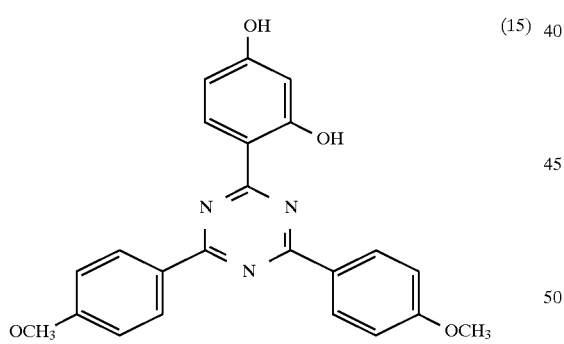
(15)
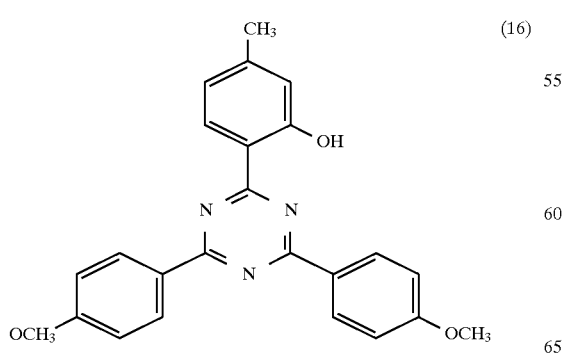
(16)
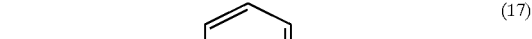
(17)
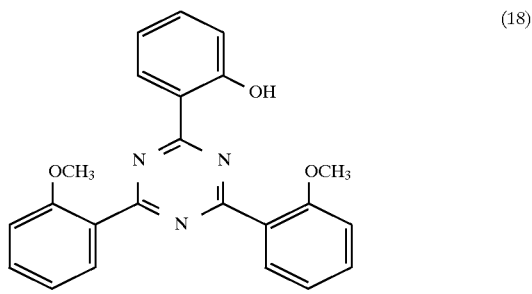
(18)
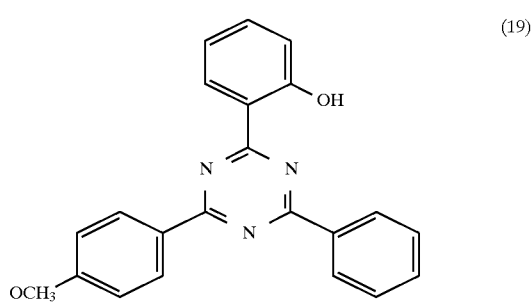
(19)
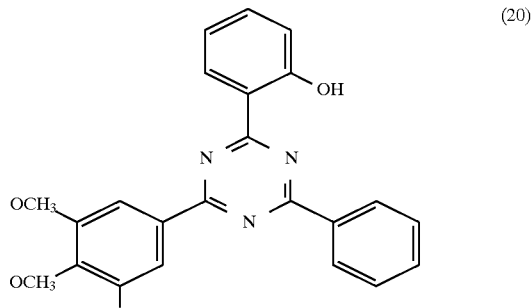
(20)
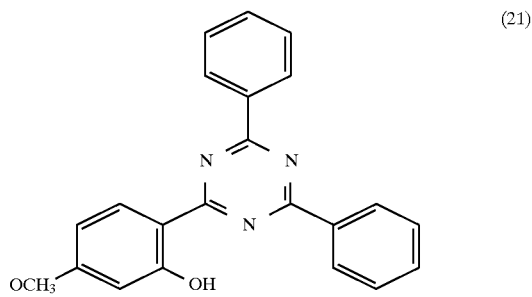
(21)

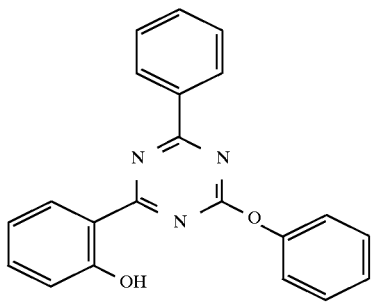

or or is 2,4,6-tris(diisobutyl-4'-aminobenzalmalonate)-s-triazine or 2,4-bis(diisobutyl-4-aminobenzalmalonate)-6-(4'-aminobenzylidenecamphor)-s-triazine.

13. A composition according to claim 1 in which the UV absorber is a triazine and has the formula:

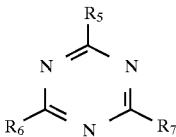

in which $R_5$, $R_6$ and $R_7$, independently, are H, OH, $C_1$–$C_{18}$alkoxy, $NH_2$, NH—$R_8$ or $N(R_8)_2$ in which $R_8$ is $C_1$–$C_{18}$alkyl, $OR_8$ in which $R_8$ has its previous significance, phenyl, phenoxy, or anilino in which the respective phenyl moieties are optionally substituted by one, two or three substitutents selected from OH, $C_1$–$C_{18}$alkyl or -alkoxy, $C_5$–$C_8$cycloalkyl, a methylidenecamphor group, a group —(CH=CH)$_n$C(=O)—$OR_8$ in which n is 0 or 1 and $R_8$ has its previous significance or a

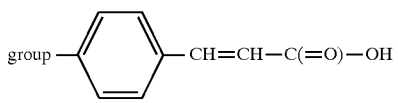

or the corresponding alkali metal, ammonium, mono-, di- or tri-$C_1$–$C_4$alkylammonium, mono-, di- or tri-$C_2$–$C_4$alkanolammonium salts, or the $C_1$–$C_{18}$alkyl esters thereof.

14. A composition according to claim 13 in which the UV absorber is a triazine having the formula:

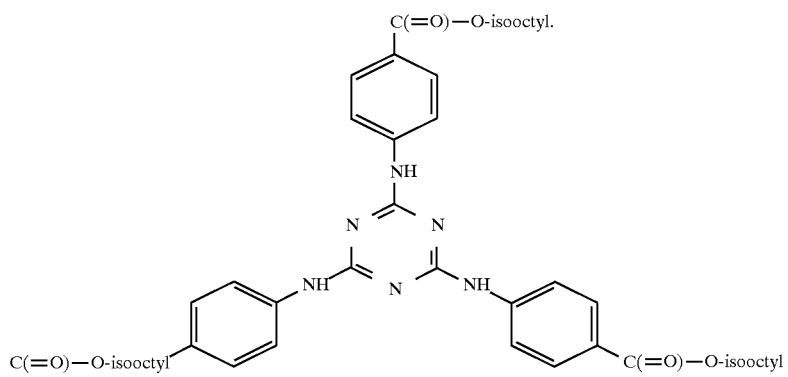

15. A composition according to claim 1 in which the UV absorber is a triazole and has the formula:

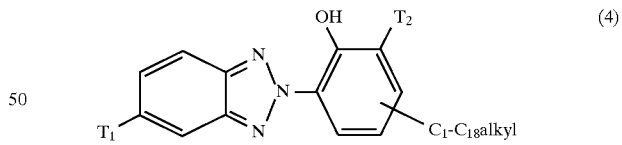

in which $T_1$ is $C_1$–$C_{18}$alkyl or hydrogen; and $T_2$ is $C_1$–$C_{18}$alkyl optionally substituted by a phenyl group.

16. A composition according to claim 15 in which $T_1$ is hydrogen.

17. A composition according to claim 16 in which the triazole has the formula:

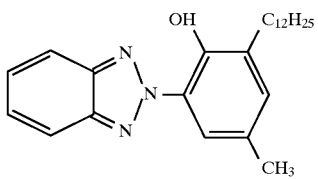

-continued

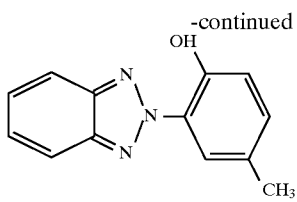
(26)

OR

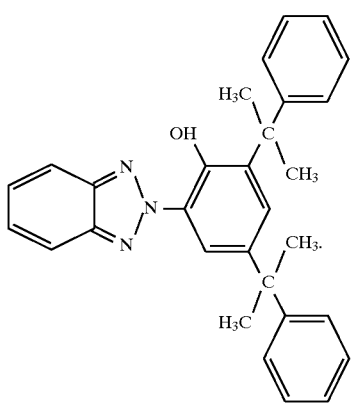
(27)

18. A composition according to claim 1 in which the UV absorber is a triazole and has the formula:

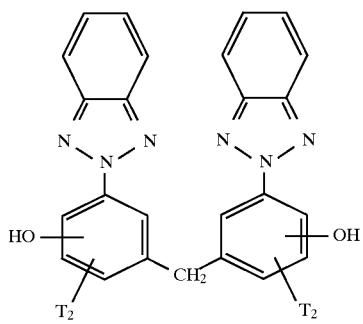
(5)

in which $T_2$ is $C_1$–$C_{18}$alkyl optionally substituted by a phenyl group.

19. A composition according to claim 18 in which the UV absorber is 2,2'-methylene-bis-[6-(2H-benzotriazol-2-yl)]4 (1,1,3,3-tetramethylbutyl)-phenyl.

20. A composition according to claim 1 in which the UV absorber is a vinyl group-containing amide UV absorber having the formula:

$$R_9\text{-}(Y)_n\text{—}C(=O)\text{—}C(R_{10})=C(R_{11})\text{—}N(R_{12})(R_{13}) \quad (6)$$

in which $R_9$ is $C_1$–$C_{18}$alkyl or phenyl in which the phenyl is optionally substituted by one, two or three substituents selected from OH, $C_1$–$C_{18}$alkyl or -alkoxy or a group —C(=O)—OR$_8$ in which $R_8$ has its previous significance; $R_{10}$ and $R_{11}$ are the same or different and each is $C_1$–$C_{18}$alkyl or hydrogen; $R_{12}$ and $R_{13}$ are the same or different and each is $C_1$–$C_{18}$alkyl or hydrogen: Y is N or O; and n is 0 or 1.

21. A composition according to claim 20 in which $R_9$ is $C_1$–$C_5$alkyl or phenyl in which the phenyl is optionally substituted by one, two or three substituents selected from OH, $C_1$–$C_{18}$alkyl or -alkoxy or a group —C(=O)—OR$_8$ in which $R_8$ is as defined in claim 18; $R_{10}$ and $R_{11}$ are the same or different and each is $C_1$–$C_5$alkyl or hydrogen; $R_{12}$ and $R_{13}$ are the same or different and each is $C_1$–$C_5$alkyl or hydrogen: Y is N or O; and n is 0 or 1.

22. A composition according to claim 21 in which the UV absorber is:

4-octylamino-3-penten-2-one
ethyl-3-octylaniino-2-butenoate
3-octylamino-1-phenyl-2-buten-1-one and
3-dodecylamino-1-phenyl-2-buten-1-one.

23. A composition according to claim 1 in which the UV absorber is a cinnamic acid amide having the formula:

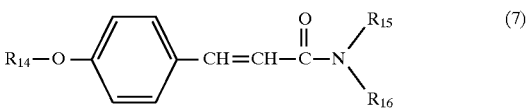
(7)

in which $R_{14}$ is hydroxy or O—$C_1$–$C_4$alkyl; $R_{15}$ is hydrogen or $C_1$–$C_4$alkyl; and $R_{16}$ is -(CONH)$_n$-phenyl in which n is 0 or 1 and the phenyl is optionally substituted by one, two or three substituents selected from OH, $C_1$–$C_{18}$alkyl or -alkoxy or a group —C(=O)—OR$_8$ in which $R_8$ is as defined in claim 18.

24. A composition according to claim 23 in which $R_{14}$ is hydroxy, methoxy or ethoxy; $R_{15}$ is hydrogen, methyl or ethyl; and $R_{16}$ is a phenyl, 4-methoxyphenyl or phenylaminocarbonyl group.

25. A sunscreen composition comprising a) 0.1 to 15% by weight of a micronised, insoluble oxalanilide, triazine, triazole, vinyl group-containing amide or cinnamic acid amide organic UV absorber having a mean particle size in the range of from 0.02 to 2.0μ; and b) a cosmetically acceptable carrier.

26. A sunscreen composition according to claim 25 comprising a) 0.5 to 10% by weight of a micronised, insoluble organic UV absorber, and b) a cosmetically acceptable carrier.

27. A composition according to claim 25 in which the micronised, insoluble organic UV absorber has been produced by grinding the insoluble organic UV absorber, in coarse particulate form, in a grinding apparatus in the presence of a grinding aid, until the insoluble organic UV absorber has been converted into micronised form.

28. A composition according to claim 27 in which the grinding apparatus is a jet, ball, vibration or hammer mill.

29. A composition according to claim 27 in which the grinding aid is used in an amount of 0.1 to 30% by weight of the insoluble organic UV absorber.

30. A composition according to claim 27 in which the grinding aid is an alkylated vinylpyrrolidone polymer, a vinylpyrrolidone-vinylacetate copolymer, an acylglutamate, an acrylate-tert.-octylpropenamide copolymer, a ditolylether sulphonic acid-formaldehyde condensate, a Carbomer, a commercial mixture of fatty acid esters comprising a nonionic precurser, or a phospholipid.

31. A composition according to claim 30 in which the grinding aid is a phospholipid.

32. A composition according to claim 31 in which the phospholipid is one or more of a phosphatidyl choline, phosphatidyl serine, phosphatidyl inositol, phosphatidyl ethanolamine, diphophatidyl glycerol or a splhingomyelin.

33. A composition according to claim 25 in which the micronised, insoluble organic UV absorber is used together with one or more UV absorbers which are conventionally used in cosmetic compositions for the protection of human skin against UV radiation.

34. A sunscreen composition according to claim 25 which is formulated as a water-in oil or an oil-in-water emulsion, an oil or oil-alcohol lotion, a vesicular dispersion of an ionic or nonionic amphiphilic lipid, an oil-alcohol or alcohol gel, a solid stick or an aerosol formulation.

35. A sunscreen composition according to claim 34 which is formulated as a water-in oil or an oil-in-water emulsion and component b) comprises 5 to 50% of an oil phase, 5 to 20% of an emulsifier and 30 to 90% of water, each by weight based on the total weight of the carrier.

36. A sunscreen composition according to claim 35 in which the oil phase comprises one or more of a hydrocarbon oil, a wax, a natural oil, a silicone oil, a fatty acid ester or a fatty alcohol.

37. A sunscreen composition according to claim 35 in which the emulsifier comprises one or more of an ethoxylated ester of a natural oil derivative; a silicone oil emulsifier; an optionally ethoxylated fatty acid soap; an ethoxylated fatty alcohol; an optionally ethoxylated sorbitan ester; an ethoxylated fatty acid; or an ethoxylated glyceride.

38. A sunscreen composition according to claim 37 in which the ethoxylated ester of a natural oil derivative is a polyethoxylated ester of hydrogenated castor oil; and the silicone oil emulsifier is silicone polyol.

39. A sunscreen composition according to claim 25 in which the sunscreen composition also comprises one or more further components selected from emollients, skin moisturisers, skin tanning accelerators, emulsion stabilisers, thickening agents, moisture retention agents, film formers, preservatives, perfumes and colourants.

40. A composition according to claim 1 which the micronised, insoluble organic UV absorber has a mean particle size in the range of from 0.05 to $1.5\mu$.

41. A composition according to claim 40 in which the micronised, insoluble organic UV absorber has a mean particle size in the range of from 0.1 to $1\mu$.

42. A composition according to claim 25 in which the micronised, insoluble organic UV absorber has a mean particle size in the range of from 0.05 to $1.5\mu$.

* * * * *